United States Patent
Mao et al.

(10) Patent No.: US 7,636,502 B2
(45) Date of Patent: Dec. 22, 2009

(54) OPTICAL WAVEGUIDE BIO-SENSING DEVICE

(75) Inventors: Yen-Chieh Mao, Kaohsiung (TW); Jian-Shian Lin, Yilan (TW); Lai-Sheng Chen, Hsinchu (TW); Wei-Han Wang, Xindian (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/540,972

(22) Filed: Oct. 2, 2006

(65) Prior Publication Data

US 2007/0147727 A1 Jun. 28, 2007

(30) Foreign Application Priority Data

Dec. 16, 2005 (TW) ............................ 94144620

(51) Int. Cl.
*G02B 6/00* (2006.01)
*G02B 6/34* (2006.01)
(52) U.S. Cl. .................................. 385/12; 385/37
(58) Field of Classification Search ............... 385/37, 385/12
See application file for complete search history.

(56) References Cited

U.S. PATENT DOCUMENTS

| 6,483,096 | B1 | 11/2002 | Kunz et al. | 250/214 R |
| 7,027,163 | B2* | 4/2006 | Angeley | 356/521 |
| 2003/0068657 | A1 | 4/2003 | Lin et al. | 435/7.9 |
| 2005/0068543 | A1* | 3/2005 | Angeley | 356/521 |
| 2006/0039647 | A1* | 2/2006 | Ling et al. | 385/24 |
| 2007/0122077 | A1* | 5/2007 | Bellman et al. | 385/37 |

* cited by examiner

*Primary Examiner*—Uyen-Chau N Le
*Assistant Examiner*—Rhonda S Peace
(74) *Attorney, Agent, or Firm*—WPAT, PC; Justin King (57) ABSTRACT

An optical waveguide bio-sensing device, comprising: a monochromatic light source, a beam splitter, a grating chip with a sub-wavelength grating structure and a sensor. Moreover, in order to enhance the sensitivity of the system using the optical waveguide bio-sensing device, a light concentrating element or a quarter waveplate ($\frac{1}{4}\lambda$) is arranged in the optical path during detection. When the grating chip is not coated with a layer of biochemical substance corresponding to a monochrome light emitted from the monochromatic light source, a reflected light of a specific narrow wavelength is reflected by a specific angle as a surface plasmon resonant effect caused by waveguide coupling is excited by the incidence of the monochrome light to the grating chip through the beam splitter; otherwise, there will be little or no reflection. Accordingly, the optical waveguide bio-sensing device can detect bio-molecular interactions, reaction rate and/or molecular dynamics without any labeling in real time. Optical systems using the present invention are simplified and capable of being portable. Thus a high sensitivity detection technique is achieved.

25 Claims, 8 Drawing Sheets

OPTICAL WAVEGUIDE BIO-SENSING DEVICE

BACKGROUND OF THE INVENTION

1. Field of the Invention

The present invention generally relates to an optical waveguide bio-sensing device and, more particularly, to an optical waveguide bio-sensing device using a grating chip with a sub-wavelength grating to serve as a platform for molecular interaction so as to detect bio-molecular interactions, reaction rate and/or molecular dynamics without any labeling in real time. Optical systems using the present invention are simplified and capable of being portable. Thus a high sensitivity detection technique is achieved.

2. Description of the Prior Art

Bio-technology is regarded as the most important field of research and the most potential industry that most countries have put emphasis upon. Bio-technology includes agricultural bio-technology, bio-pharmaceutical technology and genomic and therefore it is crucial in pharmaceutics, genomics and proteomics.

In bio-molecular interaction analysis (BIA), bio-chips have attracted tremendous attention from genomics into proteomics. Bio-chips are used to detect genetic performance and bio-molecular messages. The current detection is done mainly by fluorescence detection. In fluorescence detection, problems related to complicated fluorescence tags, difficulty in molecule tags, inevitable fluorescence decay and unavailability in dynamics information of real-time interaction occur. Therefore, a label-free detecting method is required. In 1902, R. W. Wood discovered exceptional reflection gratings. Afterwards, theoretical reports and experiments on various grating structures such as guided-mode resonant sub-wavelength gratings were found in literature.

In U.S. Pat. No. 6,483,096 entitled "Integrated-optical chemical and biochemical sensor", it is disclosed a biochemical sensing technology for molecular detection by using the tunable laser diode and the phase-locked loop (PLL) technique. However, the tunable laser diode provides a narrower range of wavelength and thus a high-precision goniometer is required so as to couple the incident light into the waveguide at a correct angle for resonance coupling.

Furthermore, in U.S. Patent Application Doc. No. 20030068657 entitled "Label-free methods for performing assays using a colorimetric resonant reflectance optical biosensor", it is disclosed a label-free methods for performing assays using a calorimetric resonant reflectance optical biosensor. In this method, a grating is provided on a molecular detection platform for molecular implantation. Monochromatic light appears after light passes the grating. A sample to be tested is disposed on the platform and is then illuminated by a white light beam. The wavelength of the incident light is changed after reflection because the molecules of the tested sample are bound to react with receptors on the grating. The change in wavelength can be detected by a spectrum analyzer so as to measure the thickness of the protein without using a probe for detecting fluorescence as well as radioactive tags. However, the reflectance spectrum exhibits a wide FWHM (full width at half magnitude) leading to a poor wavelength resolution so that detection in physiology concentration is unavailable.

Therefore, to overcome the aforementioned shortcomings, there is need in providing an optical waveguide bio-sensing device so as to detect bio-molecular interactions, reaction rate and/or molecular dynamics without any labeling in real time.

SUMMARY OF THE INVENTION

It is a primary object of the present invention to provide an optical waveguide bio-sensing device, using a grating chip with a sub-wavelength grating to serve as a platform for molecular interaction so as to detect bio-molecular interactions, reaction rate and/or molecular dynamics without any labeling in real time. Optical systems using the present invention are simplified and capable of being portable. Thus a high sensitivity detection technique is achieved.

In order to achieve the foregoing object, the present invention provides an optical waveguide bio-sensing device, comprising: a monochromatic light source, a beam splitter, a grating chip with a sub-wavelength grating structure and a sensor. Moreover, in order to enhance the sensitivity of the system using the optical waveguide bio-sensing device, a light concentrating element or a quarter waveplate (¼λ) is arranged in the optical path during detection. When the grating chip is not coated with a layer of biochemical substance corresponding to a monochrome light emitted from the monochromatic light source, a reflected light of a specific narrow wavelength is reflected by a specific angle as a surface plasmon resonant effect caused by waveguide coupling is excited by the incidence of the monochrome light to the grating chip through the beam splitter; otherwise, there will be little or no reflection.

Preferably, the wavelength of the light source is within a range from 200 nm to 1700 nm.

Preferably, the light source is a laser source or a semiconductor light source.

Preferably, the grating structure has a depth and a linewidth both within a range from 50 nm to 2 μm.

Preferably, the grating chip comprises at least a low refractive index grating structure and a waveguide layer.

Preferably, the high refractive index waveguide layer comprises at least one of silicon nitride, gallium nitride, tantalum oxide, indium-tin oxide, indium-gallium arsenide, gallium arsenide, indium phosphide, gallium arsenide-antimonide, magnesium fluoride, zinc sulfide, zinc telluride, beryllium-zinc telluride, magnesium selenide, aluminum-gallium nitride, aurum, argentum, sulfhydryl (HS), amine ($NH_2$), aldehyde (CHO), carboxyl (COOH), biotin and combination thereof.

Preferably, the grating chip comprises grating structures on both the top surface and the bottom surface.

Preferably, the optical waveguide bio-sensing device further comprises a light concentrating element.

Preferably, the light concentrating element is disposed between the light source and the grating chip.

Preferably, the light concentrating element is disposed between the grating chip and the sensor.

Preferably, the light concentrating element is a concentrating lens.

Preferably, the optical waveguide bio-sensing device further comprises a quarter waveplate.

Preferably, the quarter waveplate is disposed between the light source and the grating chip.

Preferably, the quarter waveplate is disposed on the beam splitter.

Preferably, the light concentrating element is a concentrating lens or an equivalent lens with a Fresnel surface.

In order to achieve the foregoing object, the present invention further provides an optical waveguide bio-sensing device, comprising: a monochromatic light source, a grating chip with a sub-wavelength grating structure and a sensor. The sensor is disposed opposite to the light source with the grating chip in-between. When the grating chip is not coated with a layer of biochemical substance corresponding to a monochrome light emitted from the monochromatic light source, the sensor detects no transmitting light so as to determine the grating chip is not bounded with bio-molecules; otherwise, the sensor detects transmitting light.

BRIEF DESCRIPTION OF THE DRAWINGS

The objects, spirits and advantages of the preferred embodiments of the present invention will be readily understood by the accompanying drawings and detailed descriptions, wherein.

DETAILED DESCRIPTION OF THE PREFERRED EMBODIMENT

The present invention providing an optical waveguide bio-sensing device can be exemplified by the preferred embodiments as described hereinafter.

Figure 1:
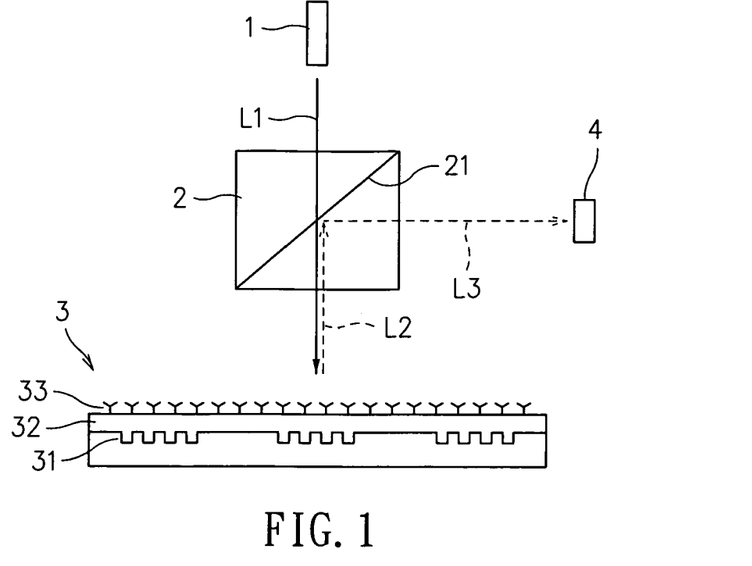
FIG. 1 is a schematic diagram showing an optical waveguide bio-sensing device wherein the grating chip is not bounded with any bio-molecule according to a first embodiment of the present invention.
Figure 1A:
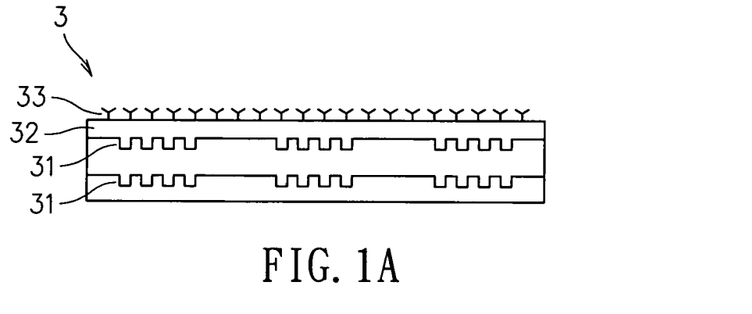
FIG. 1A shows another embodiment of the grating chip.
Figure 1B:
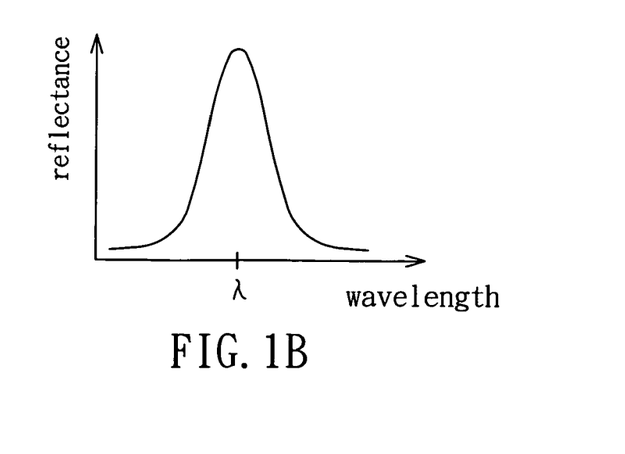
FIG. 1B shows the relation between the wavelength λ and the reflectance.

Please refer to FIG. 1, which is a schematic diagram showing an optical waveguide bio-sensing device wherein the grating chip not bounded with any bio-molecule according to a first embodiment of the present invention. The optical waveguide bio-sensing device comprises a light source 1, a beam splitter 2, a grating chip 3 and a sensor 4. In the present invention, the light source 1 is a monochromatic laser or semiconductor light source with a wavelength λ within a range from 200 nm to 1700 nm. The beam splitter 2 with polarization is disposed on the optical path so that the monochromatic light with a wavelength λ travels through the beam splitter 2 and reaches the grating chip 3. The grating structure 3 comprising at least a grating structure 31 and a waveguide layer 32 on the grating structure 31 for receiving the monochromatic light split by the beam splitter 2, wherein a receptor 33 is provided on the waveguide layer 32. The grating structure 31 is a low refractive index grating structure. The grating structure 31 is preferably designed to have a depth and a line-width both within a range from 50 nm to 2 μm. The grating structure 31 is formed on the light projecting surface of the grating chip 3. As shown in FIG. 1, the light projecting surface is the top surface of the grating chip 3. Alternatively, as shown in FIG. 1A, the grating structure 31 can also be disposed on each of the two surfaces of the grating chip 3 for two sensors 4. In the present embodiment, the waveguide layer 32 is a high refractive index material comprising at least one of silicon nitride, gallium nitride, tantalum oxide, indium-tin oxide, indium-gallium arsenide, gallium arsenide, indium phosphide, gallium arsenide-antimonide, magnesium fluoride, zinc sulfide, zinc telluride, beryllium-zinc telluride, magnesium selenide, aluminum-gallium nitride, aurum, argentum, sulfhydryl (HS), amine ($NH_2$), aldehyde (CHO), carboxyl (COOH), biotin and combination thereof. Moreover, at least a receptor 33 is provided to be combined with a substance under examination so as to change the optical characteristics of the grating chip 3 and achieve bio-sensing. The sensor 4 is disposed on the optical path of the reflected light so as to determine whether the beam splitter 2 reflects the reflected light.

As shown in FIG. 1, a monochromatic light L1 emitted from the light source 1 travels through the beam splitter 2 and reaches the grating chip 3. When the grating chip 3 is not coated with bio-molecules under examination, the waveguide resonant structure on the grating chip 3 is not affected. Therefore, a reflected light L2 of a specific narrow wavelength λ is reflected by a specific angle as a surface plasmon resonant effect caused by waveguide coupling is excited by the incidence of the monochrome light L1 to the grating chip 3 through the beam splitter 2. The reflected light L2 reaches the beam splitter 2 and is reflected by a reflecting surface 21 so that a reflected light L3 appears to reach the sensor 4. The sensor 4 detects the reflected light L3 so as to determine that the grating chip 3 is not bounded with bio-molecules. The relation between the wavelength λ and the reflectance is shown in FIG. 1A.

Figure 2:
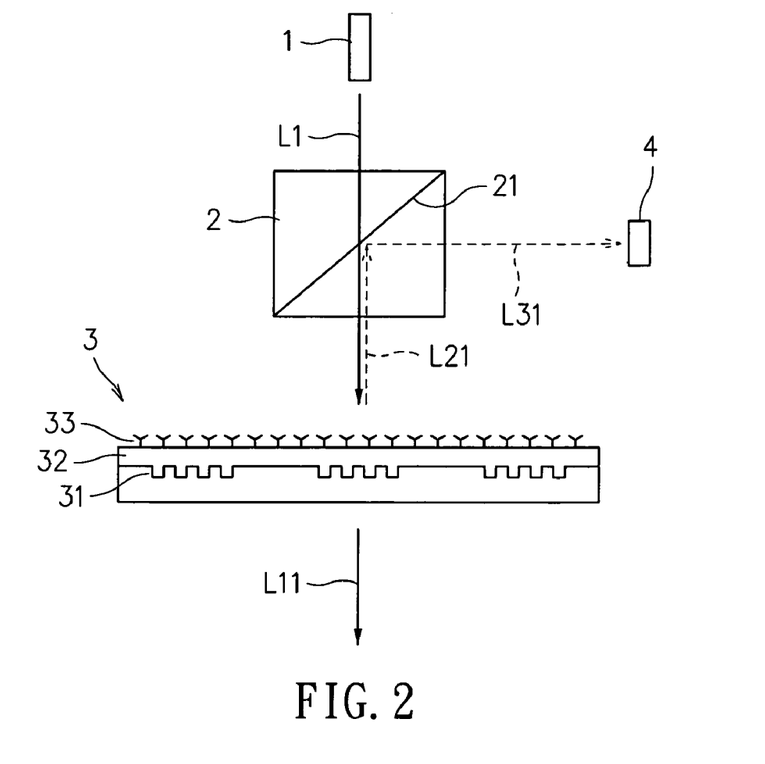
FIG. 2 is a schematic diagram showing an optical waveguide bio-sensing device wherein the grating chip is bounded with bio-molecules according to the optical waveguide bio-sensing device in FIG. 1.
Figure 2A:
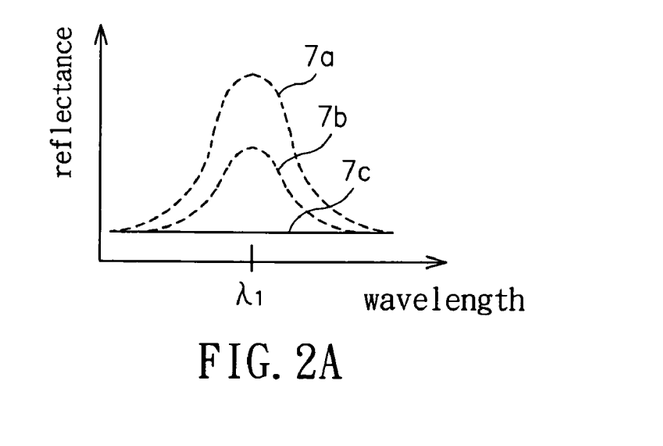
FIG. 2A shows the relation between the wavelength λ+Δλ and the reflectance after bio-molecular bounding.

Referring to FIG. 2, the monochromatic light L1 emitted from the light source 1 travels through the beam splitter 2 and reaches the grating chip 3. When the grating chip 3 is coated with bio-molecules under examination, the waveguide resonant structure on the grating chip 3 is affected so as to cause the change in optical wave vector, resulting in a shifted wavelength (for example, $\lambda+\Delta\lambda$). Little or no reflected light appears after the monochrome light L1 reaches the grating chip 3. As the intensity of the reflected light L31 detected by the sensor 4 is lowered, it is determined that the grating chip 3 is bounded with bio-molecules. As shown in FIG. 2A, 7a represents the curve in FIG. 1, 7b represents the reflected light L31 with a reduced intensity and 7c represents the reflected light L31 with an intensity reduced to zero.

Figure 3:
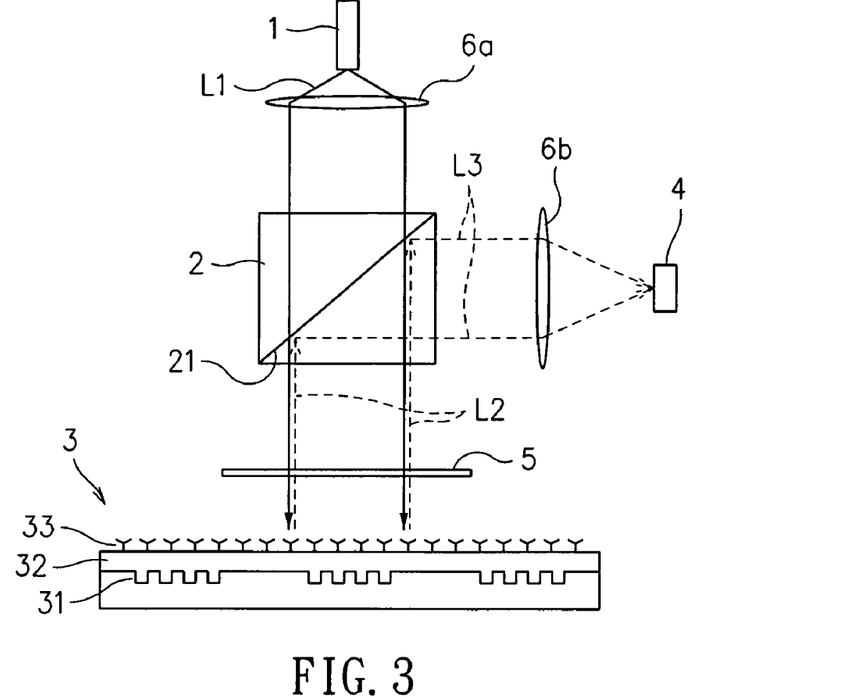
FIG. 3 is a schematic diagram showing an optical waveguide bio-sensing device wherein the grating chip is not not bounded with any bio-molecule according to a second embodiment of the present invention.

Please refer to FIG. 3, which is a schematic diagram showing an optical waveguide bio-sensing device wherein the grating chip is not bounded with any bio-molecule according to a second embodiment of the present invention. The optical waveguide bio-sensing device comprises a light source 1, a beam splitter 2, a grating chip 3 and a sensor 4. In the present embodiment, a first light concentrating element 6a is disposed between the light source 1 and the beam splitter 2 for light concentration and a second light concentrating element 6b is disposed between the grating chip 3 and the sensor 4 for light concentration. The light concentrating elements 6a and 6b can be implemented using lenses with light concentration. Moreover, in order to enhance the sensitivity of the system using the optical waveguide bio-sensing device, a quarter waveplate ($\frac{1}{4}\lambda$) 5 is arranged in the optical path between the beam splitter 2 and the grating chip 3.

Figure 3A:
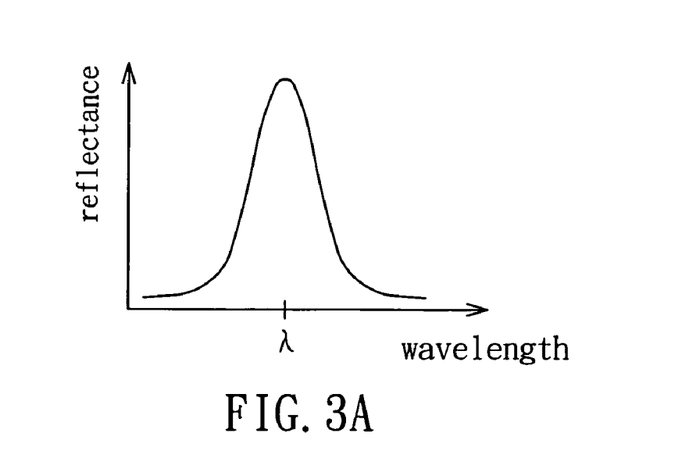
FIG. 3A shows the relation between the wavelength λ and the reflectance.

Therefore, the monochromatic light L1 emitted from the light source 1 is concentrated by the first light concentrating element 6a and then travels through the beam splitter 2 and the quarter waveplate ($\frac{1}{4}\lambda$) 5 before it reaches the grating chip 3. When the grating chip 3 is not coated with bio-molecules under examination, the waveguide resonant structure on the grating chip 3 is not affected. Therefore, a reflected light L2 of a specific narrow wavelength $\lambda$ is reflected by a specific angle as a surface plasmon resonant effect caused by waveguide coupling is excited by the incidence of the monochrome light L1. The reflected light L2 travels through the quarter waveplate ($\frac{1}{4}\lambda$) 5 and reaches the beam splitter 2 before it is reflected by a reflecting surface 21 so that a reflected light L3 appears to pass through the second light concentrating element 6b before it reaches the sensor 4. The sensor 4 detects the reflected light L3 so as to determine that the grating chip 3 is not bounded with bio-molecules. The relation between the wavelength $\lambda$ and the reflectance is shown in FIG. 3A.

Figure 4:
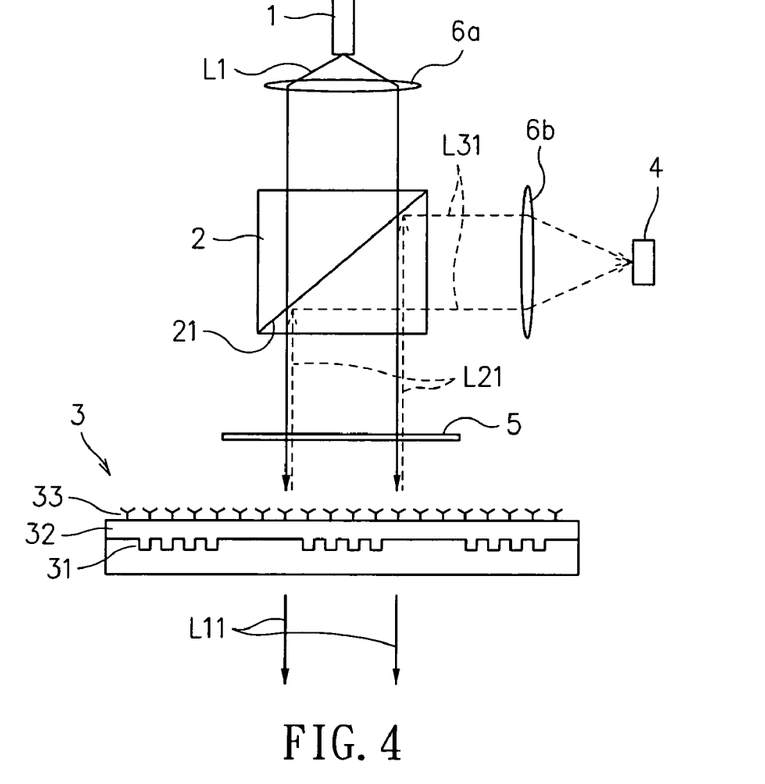
FIG. 4 is a schematic diagram showing an optical waveguide bio-sensing device wherein the grating chip is bounded with bio-molecules according to the optical waveguide bio-sensing device in FIG. 3.
Figure 4A:
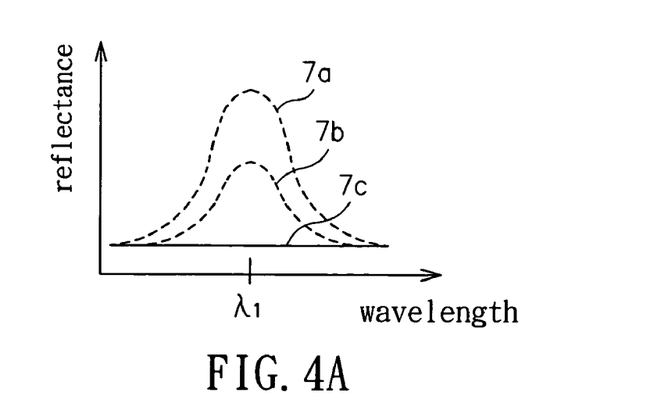
FIG. 4A shows the relation between the wavelength λ+Δλ and the reflectance after bio-molecular bounding.

Referring to FIG. 4, the monochromatic light L1 emitted from the light source 1 is concentrated by the first light concentrating element 6a and then travels through the beam splitter 2 and the quarter waveplate ($\frac{1}{4}\lambda$) 5 before it reaches the grating chip 3. When the grating chip 3 is coated with bio-molecules under examination, the waveguide resonant structure on the grating chip 3 is affected so as to cause the change in optical wave vector, resulting in a shifted wavelength $\lambda+\Delta\lambda$. Little or no reflected light appears after the monochrome light L1 reaches the grating chip 3. As the intensity of the reflected light L31 detected by the sensor 4 is lowered, it is determined that the grating chip 3 is bounded with bio-molecules. As shown in FIG. 4A, 7a represents the curve in FIG. 1, 7b represents the reflected light L31 with a reduced intensity and 7c represents the reflected light L31 with an intensity reduced to zero.

Figure 5:
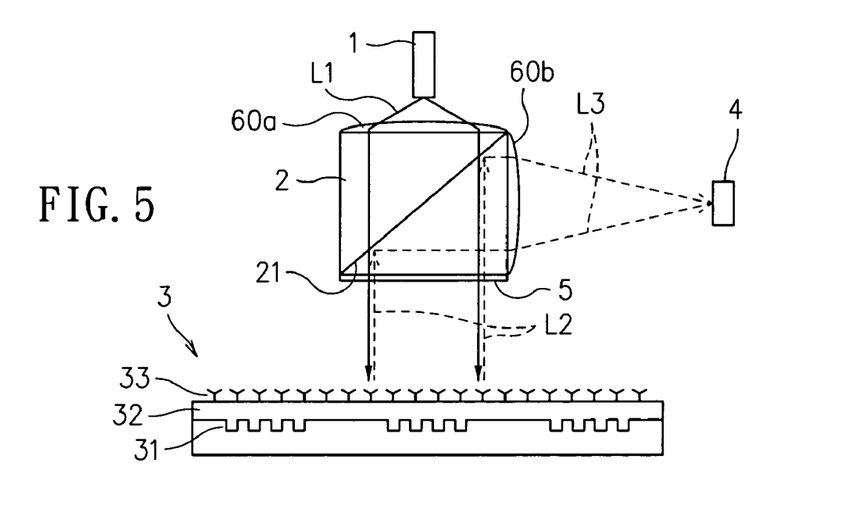
FIG. 5 is a schematic diagram showing an optical waveguide bio-sensing device wherein the grating chip is not bounded with any bio-molecule according to a third embodiment of the present invention.
Figure 5A:
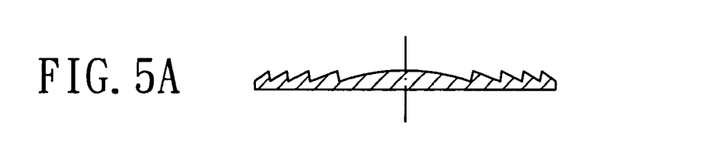
FIG. 5A shows a cross-sectional view of a Fresnel surface.

Please refer to FIG. 5, which is a schematic diagram showing an optical waveguide bio-sensing device wherein the grating chip is not bounded with any bio-molecule according to a third embodiment of the present invention. The optical waveguide bio-sensing device comprises a light source 1, a beam splitter 2, a grating chip 3, a sensor 4, a quarter waveplate 5 and light concentrating elements 60a and 60b. In the present embodiment, and quarter waveplate 5 and light concentrating elements 60a and 60b are disposed on the surfaces of the beam splitter 2. The quarter waveplate 5 is a planar surface with polarization and the light concentrating elements 60a and 60b are Fresnel surfaces with light concentration. Referring to FIG. 5A for a cross-sectional view of a Fresnel surface, the Fresnel surface comprises a plurality of concentric circular ridges. These circular ridges give the Fresnel surface a zigzag or sawtooth cross-section. Each sawtooth creates a tiny prism. By choosing appropriate powers for these prisms, designers can define the focal length and control image quality.

Therefore, the monochromatic light L1 emitted from the light source 1 is concentrated by the first light concentrating element 60a and then travels through the beam splitter 2 and the quarter waveplate 5 before it reaches the grating chip 3. When the grating chip 3 is not coated with bio-molecules under examination, the waveguide resonant structure on the grating chip 3 is not affected. Therefore, a reflected light L2 of a specific narrow wavelength $\lambda$ is reflected by a specific angle as a surface plasmon resonant effect caused by waveguide coupling is excited by the incidence of the monochrome light L1. The reflected light L2 travels through the quarter waveplate 5 and reaches the beam splitter 2 before it is reflected by a reflecting surface 21 so that a reflected light L3 appears to pass through the second light concentrating element 60b before it reaches the sensor 4. The sensor 4 detects the reflected light L3 so as to determine that the grating chip 3 is not bounded with bio-molecules. The relation between the wavelength $\lambda$ and the reflectance is shown in FIG. 3A.

Figure 6:
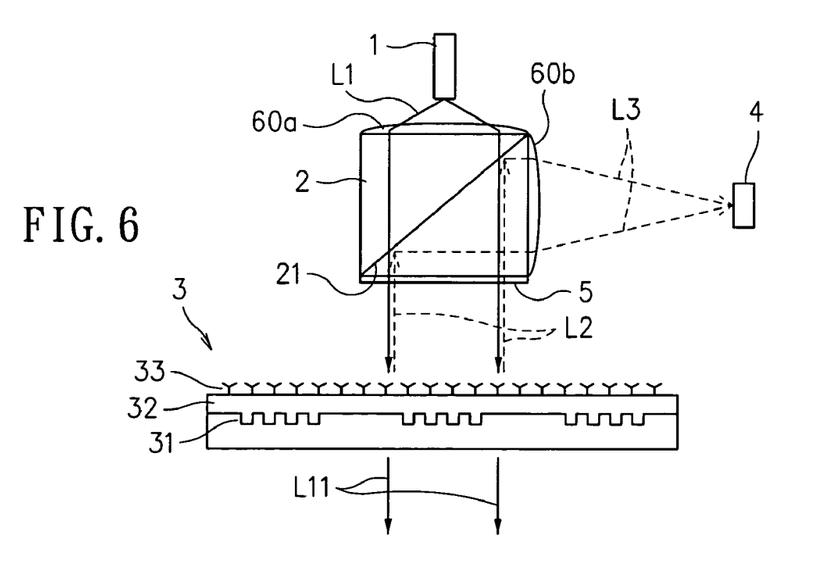
FIG. 6 is a schematic diagram showing an optical waveguide bio-sensing device wherein the grating chip is bounded with bio-molecules according to the optical waveguide bio-sensing device in FIG. 5.

Referring to FIG. 6, the monochromatic light L1 emitted from the light source 1 is concentrated by the first light concentrating element 60a and then travels through the beam splitter 2 and the quarter waveplate 5 before it reaches the grating chip 3. When the grating chip 3 is coated with bio-molecules under examination, the waveguide resonant structure on the grating chip 3 is affected so as to cause the change in optical wave vector, resulting in a shifted wavelength $\lambda+\Delta\lambda$. Little or no reflected light appears after the monochrome light L1 reaches the grating chip 3. As the intensity of the reflected light L31 detected by the sensor 4 is lowered, it is determined that the grating chip 3 is bounded with bio-molecules. The relation between the wavelength $\lambda+\Delta\lambda$ and the reflectance is shown in FIG. 4A.

According to the first, second and third embodiments of the present invention, a conclusion is made to summarize a method for bio-sensing, which comprises steps of:

(a) emitting a monochromatic light L1 from a light source 1;

(b) passing the monochromatic light L1 through a beam splitter 2 to a grating chip 3; and (c) detecting the intensity of a reflected light L3 1 by a sensor 4.

Figure 7:
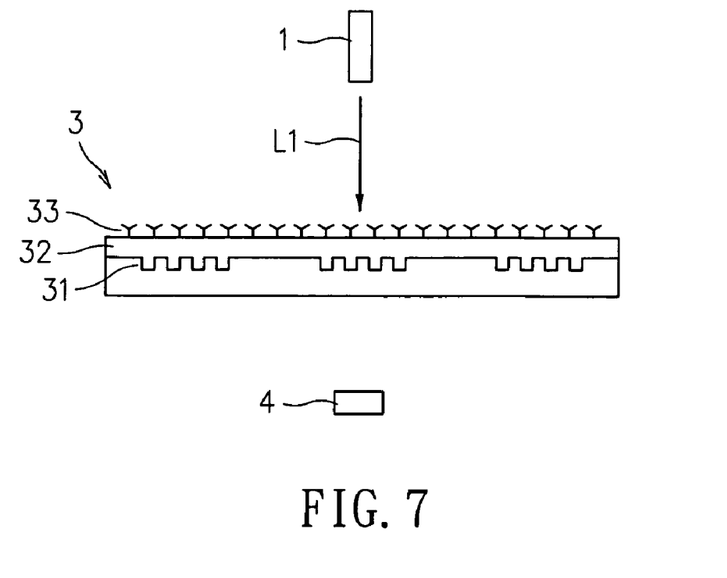
FIG. 7 is a schematic diagram showing an optical waveguide bio-sensing device wherein the grating chip is not not bounded with any bio-molecule according to a fourth embodiment of the present invention.

Please refer to FIG. 7, which is a schematic diagram showing an optical waveguide bio-sensing device wherein the grating chip is not bounded with any bio-molecule according to a fourth embodiment of the present invention. The optical waveguide bio-sensing device comprises a light source 1, a grating chip 3 and a sensor 4. In the present embodiment, the sensor 4 is disposed opposite to the light source 1 with the grating chip 3 in-between. When the grating chip 3 is not coated with bio-molecules under examination, a reflected light L2 is reflected by a specific angle as a surface plasmon resonant effect caused by waveguide coupling is excited by the incidence of the monochrome light L1. Therefore, the sensor 4 does not detect any transmitting light so as to determine that the grating chip 3 is not bounded with bio-molecules.

Figure 8:
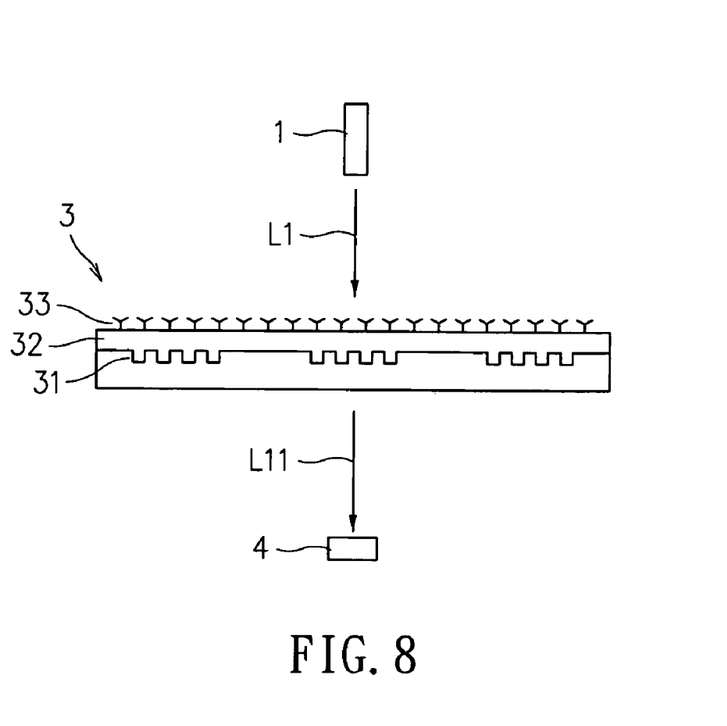
FIG. 8 is a schematic diagram showing an optical waveguide bio-sensing device wherein the grating chip is bounded with bio-molecules according to the optical waveguide bib-sensing device in FIG. 7.

Referring to FIG. 8, when the grating chip 3 is coated with bio-molecules under examination, the monochromatic light L1 transmits through the grating chip 3 so that the sensor 4 detects a transmitting light L11. Accordingly, it is determined that the grating chip 3 is bounded with bio-molecules.

Figure 9:
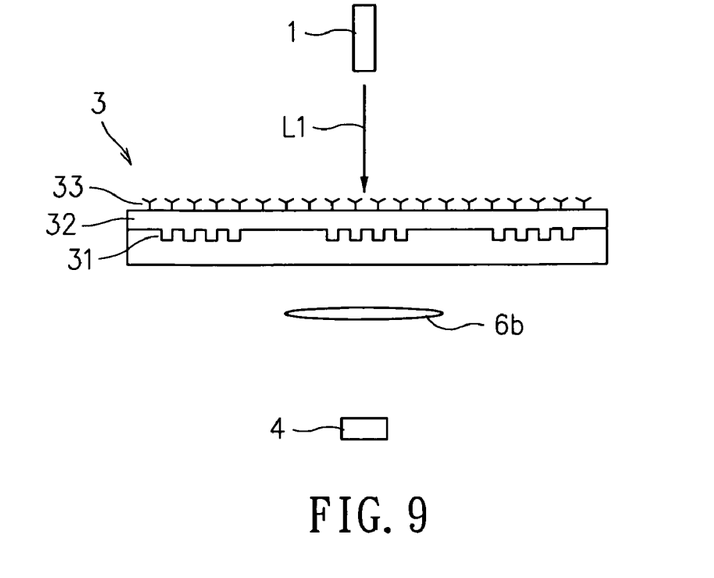
FIG. 9 is a schematic diagram showing an optical waveguide bio-sensing device wherein the grating chip is not not bounded with any bio-molecule according to a fifth embodiment of the present invention.

Please refer to FIG. 9, which is a schematic diagram showing an optical waveguide bio-sensing device wherein the grating chip is not bounded with any bio-molecule according to a fifth embodiment of the present invention. The optical waveguide bio-sensing device comprises a light source 1, a grating chip 3 and a sensor 4. In the present embodiment, a concentrating element 6b is disposed between the grating chip 3 and the sensor 4 for light concentration. The light concentrating element is a concentrating lens or an equivalent lens with a Fresnel surface.

When the grating chip 3 is not coated with bio-molecules under examination, a reflected light L2 is reflected by a specific angle as a surface plasmon resonant effect caused by waveguide coupling is excited by the incidence of the monochrome light L1. Therefore, the sensor 4 does not detect any transmitting light so as to determine that the grating chip 3 is not bounded with bio-molecules.

Figure 10:
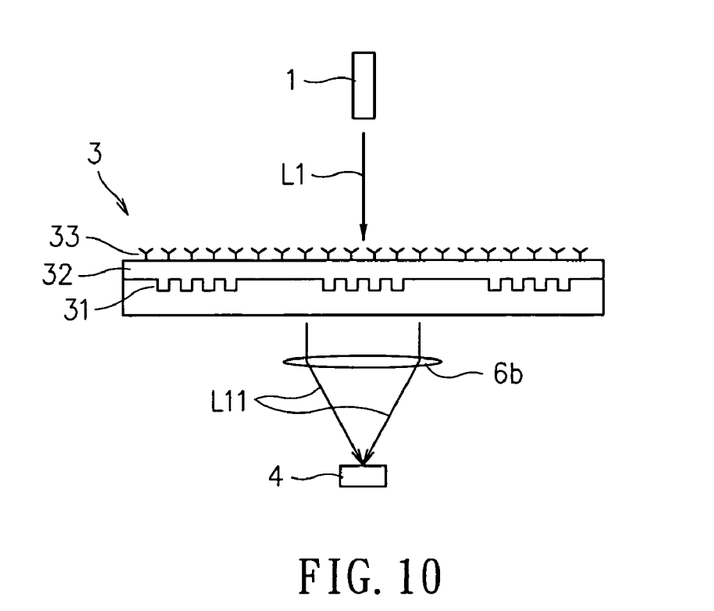
FIG. 10 is a schematic diagram showing an optical waveguide bio-sensing device wherein the grating chip is bounded with bio-molecules according to the optical waveguide bio-sensing device in FIG. 9.

Referring to FIG. 10, when the grating chip 3 is coated with bio-molecules under examination, the monochromatic light L1 transmits through the grating chip 3 so that the sensor 4 detects a transmitting light L11. Accordingly, it is determined that the grating chip 3 is bounded with bio-molecules.

Figure 11:
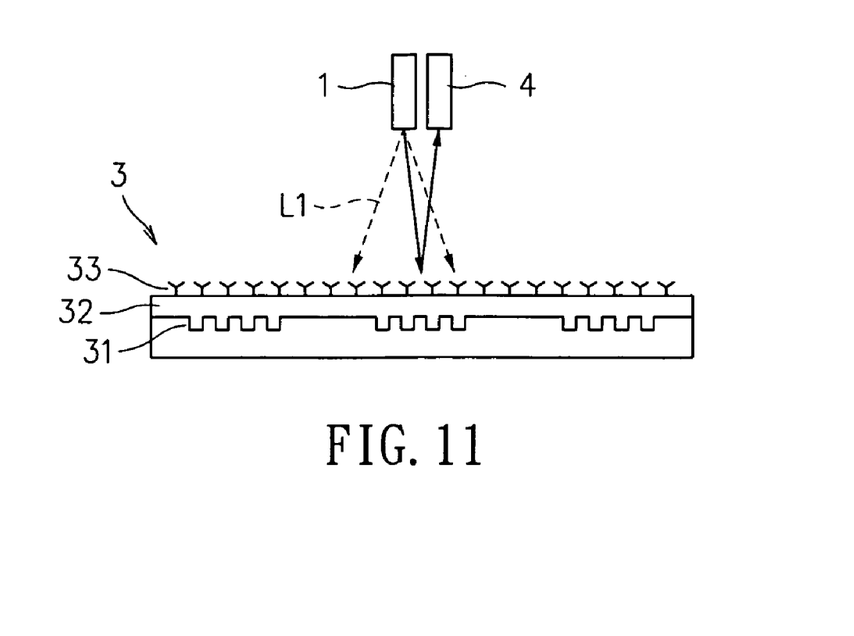
FIG. 11 is a schematic diagram showing an optical waveguide bio-sensing device according to a sixth embodiment of the present invention.
Figure 11A:
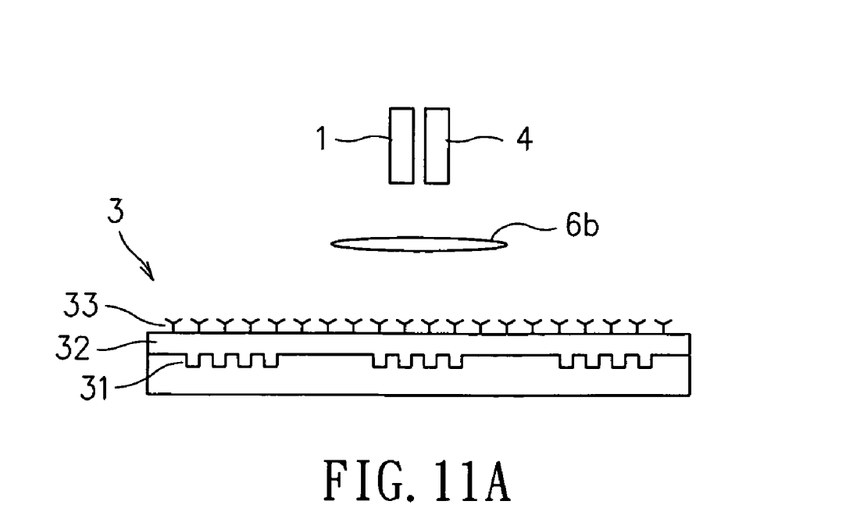
FIG. 11A is a schematic diagram showing an optical waveguide bio-sensing device according to a seventh embodiment of the present invention.

Please refer to FIG. 11 and FIG. 11A, which are schematic diagrams showing optical waveguide bio-sensing devices according to a sixth and a seventh embodiments of the present invention. In FIG. 11, the optical waveguide bio-sensing device is similar to that in FIG. 7 except that, in FIG. 11, the sensor 4 is installed on the same side of the grating chip 3 as the light source 1. However, in FIG. 11A, a light concentrating element 6b is disposed between the light source 1 with the sensor 4 and the grating chip 3. The implementations and operations of the optical waveguide bio-sensing devices in FIG. 11 and FIG. 11A are similar to the previous embodiment, and description thereof is omitted.

According to the fourth and fifth embodiments of the present invention, a conclusion is made to summarize a method for bio-sensing, which comprises steps of:

(a) emitting a monochromatic light L1 from a light source 1;

(b) passing the monochromatic light L1 to a grating chip 3; and (c) detecting the intensity of a transmitting light L11 by a sensor 4.

Therefore, it is apparent that the present invention discloses an optical waveguide bio-sensing device using a grating chip with a sub-wavelength grating to serve as a platform for molecular interaction so as to detect bio-molecular interactions, reaction rate and/or molecular dynamics without any labeling in real time. Optical systems using the present invention are simplified and capable of being portable. Thus a high sensitivity detection technique is achieved. The present invention is novel, useful and non-obvious.

Although this invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. An optical waveguide bio-sensing device, comprising:
a light source, capable of emitting a monochromatic light;
a grating chip, comprising at least a grating structure and a waveguide layer on the grating structure for receiving the monochromatic light, wherein a receptor is provided on the waveguide layer and a sample substance is coated on the grating chip;
a beam splitter, disposed between the light source and the grating chip for the monochromatic light to transmit therethrough or to be reflected thereby to generate a reflected light; and
a sensor, for detecting the reflected lights;
wherein the waveguide layer comprises at least one of silicon nitride, gallium nitride, tantalum oxide, indium-tin oxide, indium-gallium arsenide, gallium arsenide, indium phosphide, gallium arsenide-antimonide, magnesium fluoride, zinc sulfide, zinc telluride, beryllium-zinc telluride, magnesium selenide, aluminum-gallium nitride, aurum, argentum, sulfhydryl (HS), amine (NH2), aldehyde (CHO), carboxyl (COOH), biotin and combination thereof;
wherein the grating structure has a depth within a range from 50 nm to 2 μm and a line-width both within a range from 50 nm to 2 μm.

2. The optical waveguide bio-sensing device as recited in claim 1, wherein the light source is a laser source.

3. The optical waveguide bio-sensing device as recited in claim 1, wherein the light source comprises at least a light emitting element.

4. The optical waveguide bio-sensing device as recited in claim 1, wherein the grating chip comprises grating structures on both the top surface and the bottom surface.

5. The optical waveguide bio-sensing device as recited in claim 1, further comprising a light concentrating element.

6. The optical waveguide bio-sensing device as recited in claim 5, wherein the light concentrating element is disposed between the light source and the beam splitter, between the grating chip and the beam splitter, between the beam splitter and the sensor, or on the beam splitter.

7. The optical waveguide bio-sensing device as recited in claim 5, wherein the light concentrating element is a concentrating lens or an equivalent lens with a Fresnel surface.

8. The optical waveguide bio-sensing device as recited in claim 1, further comprising a quarter waveplate.

9. The optical waveguide bio-sensing device as recited in claim 8, wherein the quarter waveplate is disposed between the light source and the beam splitter, between the grating chip and the beam splitter, or on the beam splitter.

10. An optical waveguide bio-sensing device, comprising:
a light source, capable of emitting a monochromatic light;
a grating chip, comprising at least a grating structure and a waveguide layer on the grating structure for receiving the monochromatic light, wherein a receptor is provided on the waveguide layer and a sample substance is coated on the grating chip; and
a sensor, disposed opposite to the light source with the grating chip in-between for detecting the monochromatic light transmitting though the grating chip;
wherein the waveguide layer comprises at least one of silicon nitride, gallium nitride, tantalum oxide, indium-tin oxide, indium-gallium arsenide, gallium arsenide, indium phosphide, gallium arsenide-antimonide, magnesium fluoride, zinc sulfide, zinc telluride, beryllium-zinc telluride, magnesium selenide, aluminum-gallium nitride, aurum, argentum, sulfhydryl (HS), amine (NH2), aldehyde (CHO), carboxyl (COOH), biotin and combination thereof;

wherein the grating structure has a depth within a range from 50 nm to 2 µm and a line-width both within a range from 50 nm to 2 µm.

11. The optical waveguide bio-sensing device as recited in claim 10, wherein the light source is a laser source.

12. The optical waveguide bio-sensing device as recited in claim 10, wherein the light source comprises at least a light emitting element.

13. The optical waveguide bio-sensing device as recited in claim 10, wherein the grating chip comprises grating structures on both the top surface and the bottom surface.

14. The optical waveguide bio-sensing device as recited in claim 10, further comprising a light concentrating element.

15. The optical waveguide bio-sensing device as recited in claim 14, wherein the light concentrating element is disposed between the light source and the grating chip, or between the grating chip and the sensor.

16. The optical waveguide bio-sensing device as recited in claim 14, wherein the light concentrating element is a concentrating lens or an equivalent lens with a Fresnel surface.

17. An optical waveguide bio-sensing device, comprising:
a light source, capable of emitting a monochromatic light;
a grating chip, comprising at least a grating structure and a waveguide layer on the grating structure for receiving the monochromatic light, wherein a receptor is provided on the waveguide layer and a sample substance is coated on the grating chip; and
a sensor, disposed on the same side of the grating chip as the light source for detecting a reflected light reflected by the grating chip;
wherein the waveguide layer comprises at least one of silicon nitride, gallium nitride, tantalum oxide, indium-tin oxide, indium-gallium arsenide, gallium arsenide, indium phosphide, gallium arsenide-antimonide, magnesium fluoride, zinc sulfide, zinc telluride, beryllium-zinc telluride, magnesium selenide, aluminum-gallium nitride, aurum, argentum, sulfhydryl (HS), amine (NH2), aldehyde (CHO), carboxyl (COOH), biotin and combination thereof;

wherein the grating structure has a depth within a range from 50 nm to 2 µm and a line-width both within a range from 50 nm to 2 µm.

18. The optical waveguide bio-sensing device as recited in claim 17, wherein the light source is a laser source.

19. The optical waveguide bio-sensing device as recited in claim 17, wherein the light source comprises at least a light emitting element.

20. The optical waveguide bio-sensing device as recited in claim 17, wherein the grating chip comprises grating structures on both the top surface and the bottom surface.

21. The optical waveguide bio-sensing device as recited in claim 17, further comprising a light concentrating element.

22. The optical waveguide bio-sensing device as recited in claim 21, wherein the light concentrating element is disposed between the light source and the grating chip, or between the grating chip and the sensor.

23. The optical waveguide bio-sensing device as recited in claim 21, wherein the light concentrating element is a concentrating lens or an equivalent lens with a Fresnel surface.

24. The optical waveguide bio-sensing device as recited in claim 17, further comprising a quarter waveplate.

25. The optical waveguide bio-sensing device as recited in claim 24, wherein the quarter waveplate is disposed between the light source and the grating chip, or between the grating chip and the sensor.

* * * * *